United States Patent [19]

Kagabu et al.

[11] Patent Number: 5,360,935
[45] Date of Patent: Nov. 1, 1994

[54] PROCESS FOR THE PREPARATION OF 3-PHENYL-2-PROPENONES

[75] Inventors: Shinzo Kagabu, Gifu; Katsuaki Wada, Tochigi, both of Japan

[73] Assignee: Nihon Bayer Agrochem K.K., Tokyo, Japan

[21] Appl. No.: 944,556

[22] Filed: Sep. 14, 1992

[30] Foreign Application Priority Data

Sep. 24, 1991 [JP] Japan .................. 3-270465

[51] Int. Cl.$^5$ .................. C07C 49/683; C07C 79/798
[52] U.S. Cl. .................. 568/316; 568/312
[58] Field of Search .................. 548/546; 568/316

[56] References Cited

PUBLICATIONS

Journal of the Chemical Society, Chemical Communications 1991, Letchworth GB pp. 408–410, Shinzo Kagabu et al. 'Alkene Formation through Condensation of Phenylmethanesulphonyl Fluoride with Carbonyl Compounds'.
J. Am. Chem. Soc. 1987, 109, 7472–7477 "Nucleophilic Substitution Reaction of Phenylmethanesulfonyl Halides with Anilines".
J. Chem. Soc., Chem. Commun., 1991, 408–410, "Alkene Formation through Condensation of Phenylmethanesulphonyl Fluoride with Carbonyl Compounds".
Journal of Organic Chemistry, vol. 25, Jul.–Dec. 1960, "Synthesis of Fluorides By Metathesis With Sodium Fluoride".

Primary Examiner—David B. Springer
Attorney, Agent, or Firm—Sprung Horn Kramer & Woods

[57] ABSTRACT

A novel process for the preparation of 3-pheny-2-propenones of the formula

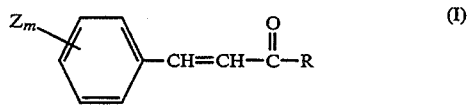

which process comprises reacting phenylmethanesulphonyl fluorides of the formula

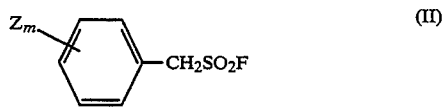

with ketones of the formula

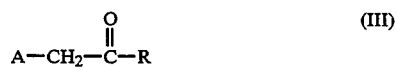

in which
A, R, Z and M have the meanings given in the specification,
in the presence of a phase transfer catalyst and in the presence of acid binders and inert solvents.

The products are known intermediates for the preparation of pesticides and pharmaceuticals.

4 Claims, No Drawings

PROCESS FOR THE PREPARATION OF 3-PHENYL-2-PROPENONES

The present invention relates to a novel process for the preparation of known 3-phenyl-2-propenones, which can be used as intermediates for the synthesis of pesticides, and pharmaceuticals.

It has already been disclosed that compounds having chalcone-type structure can in general be synthesized by condensing acetophenone with benzaldehyde in the presence of alkali. Further, arcyl-substituted alkenes can be otained by reacting phenylmethanesulphonyl fluorides with aldehydes or ketones (see J. Chem. Soc., Chem. Commun., 1991, 408–411).

It has been found now that 3-phenyl-2-propenones of the formula

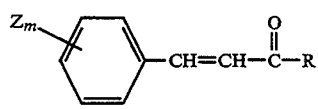 (I)

in which
Z represents halogen, nitro, alkyl, halogenoalkyl, cycloalkyl, alkoxy, halogenoalkoxy, alkylthio, halogenoalkylthio, optionally substituted phenyl, optionally substituted phenoxy, optionally substituted phenylalkyl, optionally substituted phenylalkoxy or optionally substituted phenylakenyl, R represents alkyl, optionally substituted cycloalkyl, optionally substituted phenyl, optionally substituted phenylalkyl, optionally substituted phenylalkoxy, optionally substituted phenylakenyl, optionally substituted alkoxy, optionally substituted heteroaryl, a condensed aromatic ring system or cyano, and m represents an integer 0, 1, 2, 3 or 4, are obtained when phenylmethanesulphonyl fluorides of the formula

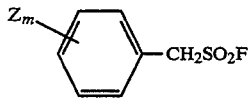 (II)

in which
Z and m have the above-mentioned meanings, are reacted with ketones of the formula

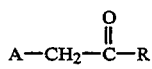 (III)

in which
R has the above-mentioned meaning and
A represents chlorine, bromine, iodine, alkylsulphonyl, phenylsulphonyl or para-tolylsulphonyl,
in the presence of a phase transfer-catalyst and in the presence of acid binders and inert solvents.

It is extremely surprising that 3-phenyl-2-propenones can be prepared by the process according to the invention in high yields and excellent purity. Based on the prior art as known from J. Chem. Soc., Chem. Commun. 1991, 408–411, one would assume the formation of phenyl-substituted alkenes through condensation at the carbonyl group. In striking contrast to such expectation, however, the presently claimed process does not proceed via an attack at the carbonyl group. Such course of reaction is indeed decidedly surprising.

The process according to the invention is distinguished by a number of advantages. Thus, the mild reaction conditions prevent a self-condensation of the ketones, which are employed as starting materials. Further, the reaction and the isolation procedures are simple. Another advantage is that the starting materials are easily available. Finally, it is noted the presently claimed process stereoselectively leads to trans-substituted propenones only.

If, for example, phenylmethanesulphonyl fluoride and phenacyl bromide are used as starting substances, the course of the process according to the invention can be illustrated by the following equation:

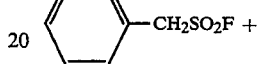

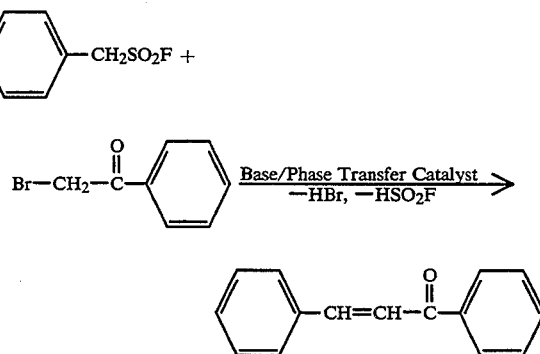

Formula (II) provides a general definition of the phenylmethanesulphonyl fluorides required as starting substances when carrying out the process according to the invention. In this formula, Z preferably represents fluorine, chlorine, bromine, nitro, straight-chain or branched alkyl with 1 to 4 carbon atoms, halogenoalkyl with 1 or 2 carbon atoms and 1 to 5 identical or different halogen atoms, such as fluorine or chlorine, or represents cycloalkyl with 5 to 7 carbon atoms, straight-chain or branched alkoxy with 1 to 4 carbon atoms, halogenoalkoxy with 1 or 2 carbon atoms and 1 to 5 identical or different halogen atoms, such as fluorine or chlorine, or represents straight-chain or branched alkylthio with 1 to 4 carbon atoms, halogenoalkylthio with 1 or 2 carbon atoms and 1 to 5 identical or different halogen atoms, such as fluorine or chlorine, or represents phenyl which is optionally mono- or disubstituted by identical or different radicals selected from halogen and/or straight chain or branched alkyl with 1 to 4 carbon atoms, or represents phenoxy which is optionally mono- or disubstituted by identical or different radicals selected from halogen and/or straight-chain or branched alkyl with 1 to 4 carbon atoms, or represents phenylalkyl with 1 or 2 carbon atoms in the alkyl group, the phenyl group being optionally mono- or disubstituted by identical or different radicals selected from halogen and/or straight-chain or branched alkyl with 1 to 4 carbon atoms, or represents phenylalkoxy with 1 or 2 carbon atoms in the alkoxy group, the phenyl group being optionally mono- or disubstituted by identical or different radicals selected from halogen and/or straight-chain or branched alkyl with 1 to 4 carbon atoms, or represents phenylalkenyl with 2 to 4 carbon atoms in the alkenyl group, the phenyl group being optionally mono- or disubstituted by identical or different radicals selected from halogen and/or straight-chain or branched alkyl with 1 to 4 carbon atoms, and m preferably represents an integer 0, 1, 2 or 3.

Particularly preferred phenylmethanesulphonyl fluorides are those compounds of the formula (II), in which Z represents fluorine, chlorine, bromine, nitro, methyl, ethyl, isopropyl, tert.-butyl, trifluoromethyl, cyclopentyl, cyclohexyl, methoxy, ethoxy, trifluoromethoxy, methylthio, ethylthio, trifluoromethylthio, phenyl which is optionally substituted by 1 or 2 identical or different radicals selected from fluorine, chlorine and/or methyl, or represents phenoxy which is optionally substituted by 1 or 2 identical or different radicals selected from fluorine, chlorine and/or methyl, or represents benzyl wherein the phenyl group is optionally substituted by 1 or 2 identical or different radicals selected from fluorine, chlorine and/or methyl, or represents benzyloxy wherein the phenyl group is optionally substituted by 1 or 2 identical or different radicals selected from fluorine, chlorine and/or methyl, or represents phenylalkenyl with 2 or 3 carbon atoms in the alkenyl group and wherein the phenyl group is optionally substituted by 1 or 2 identical or different radicals selected from fluorine, chlorine and/or methyl, and m represents an integer 0, 1 or 2.

The following compounds may be mentioned as examples of phenylmethane-sulphonyl fluorides of the formula (II):

phenylmethanesulphonyl fluoride,
4-chlorophenylmethanesulphonyl fluoride,
4-bromophenylmethanesulphonyl fluoride,
4-methylphenylmethanesulphonyl fluoride,
4-methoxyphenylmethanesulphonyl fluoride,
4-fluorophenylmethanesulphonyl fluoride,
4-trifluorophenylmethanesulphonyl fluoride,
4-nitrophenylmethanesulphonyl fluoride,
4-phenoxyphenylmethanesulphonyl fluoride,
4-phenylphenylmethanesulphonyl fluoride,
3,4-dichlorophenylmethanesulphonyl fluoride,
3-methylphenylmethanesulphonyl fluoride,
3-methoxyphenylmethanesulphonyl fluoride, and
3-fluorophenylmethanesulphonyl fluoride.

The phenylmethanesulphonyl fluorides of the formula (II) are known or can be synthesized by principally known methods (see J. Org. Chem. 25 (1960) 2016).

Formula (III) provides a general definition of the ketones, which are also required as starting substances when carrying out the process according to the invention. In this formula, R preferably represents straight-chain or branched alkyl with 1 to 4 carbon atoms, cycloalkyl with 3 to 7 carbon atoms optionally substituted by 1 to 3 identical or different alkyl radicals with 1 or 2 carbon atoms, or represents phenyl which is optionally substituted by 1 to 3 identical or different radicals selected from halogen, nitro, straight-chain or branched alkyl with 1 to 4 carbon atoms and/or halogenoalkyl with 1 or 2 carbon atoms and 1 to 5 identical or different halogen atoms, such as fluorine or chlorine, or represents phenylalkyl with 1 or 2 carbon atoms in the alkyl group, the phenyl group optionally being substituted by 1 to 3 identical or different radicals selected from halogen, straight-chain or branched alkyl with 1 to 4 carbon atoms and/or halogenoalkyl with 1 or 2 carbon atoms and 1 to 5 identical or different halogen atoms, such as fluorine or chlorine, or represents phenylalkoxy with 1 or 2 carbon atoms in the alkoxy group, the phenyl group optionally being substituted by 1 to 3 identical or different radicals selected from halogen, straight-chain or branched alkyl with 1 to 4 carbon atoms and/or halogenoalkyl with 1 or 2 carbon atoms and 1 to 5 identical or different halogen atoms, such as fluorine or chlorine, or represents phenylalkenyl with 2 to 4 carbon atoms in the alkenyl group, the phenyl group being optionally substituted by 1 to 3 identical or different radicals selected from halogen, straight-chain or branched alkyl with 1 to 4 carbon atoms and/or halogenoalkyl with 1 or 2 carbon atoms and 1 to 5 identical or different halogen atoms, such as fluorine or chlorine, or represents alkoxy with 1 to 4 carbon atoms, said alkoxy group being optionally substituted by 1 to 3 identical or different halogen atoms, or represents five- or six-membered heteraryl with 1 to 3 heteroatoms selected from oxygen, sulphur and nitrogen, the heteroaryl group being optionally substituted by 1 to 3 identical or different radicals selected from halogen and alkyl with 1 to 4 carbon atoms, or represents naphthyl, anthracenyl or cyano, and A preferably represents chlorine, bromine, iodine, alkylsulphonyl with 1 to 4 carbon atoms, phenylsulphonyl or para-tolylsulphonyl.

Particularly preferred ketones are those compounds of the formula (III), in which R represents methyl, ethyl, isopropyl, tert.-butyl, cyclopropyl optionally substituted by 1 to 3 methyl groups, cyclopentyl optionally substituted by 1 to 3 methyl groups, cyclohexyl optionally substituted by 1 to 3 methyl groups, or represents phenyl which is optionally substituted by 1 to 3 identical or different radicals selected from fluorine, chlorine, bromine, iodine, nitro, methyl and trifluoromethyl, or represents benzyl which is optionally substituted in the phenyl group by 1 or 2 identical or different radicals selected from fluorine, chlorine, methyl and trifluoromethyl, or represents benzyloxy which is optionally substituted in the phenyl group by 1 or 2 identical or different radicals selected from fluorine, chlorine, methyl and trifluoromethyl, or represents phenylalkenyl with 2 or 3 carbon atoms in the alkenyl group, the phenyl group being optionally substituted by 1 or 2 identical or different radicals selected from fluorine, chlorine, methyl and trifluoromethyl, or represents alkoxy with 1 or 2 carbon atoms, or represents furyl, thienyl, pyrrolyl, pyridinyl, pyrimidinyl or pyrazinyl, each of said six last-mentioned radicals being optionally substituted by 1 or 2 substituents selected from chlorine and methyl, or represents naphthyl, anthracenyl or cyano, and A represents chlorine, bromine, iodine, methylsulphonyl, phenylsulphonyl or para-tolylsulphonyl.

The following compounds may be mentioned as examples of the ketones of the formula (III):
phenacyl bromide,
4-chlorophenacyl bromide,
4-bromophenacyl bromide,
4-nitrophenacyl bromide, 4-fluorophenacyl bromide, and
3,4-dichlorophenacyl bromide.

The ketones of the formula (III) are known or can be prepared by generally known methods.

Suitable phase transfer catalysts for carrying out the process according to the invention are tetraalkyl ammonium halides, benzylakyl ammonium halides, benzylammonium halides, tetraalkyl phosphonium halides, crown ethers and cryptands, such as the compounds of the formulae

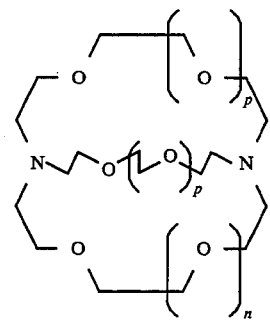

p = n = 0; [1,1,1]
p = 0, n = 1; [1,1,2]
p = n = 1; [2,2,2]
p = 1, n = 0; [2,2,1]

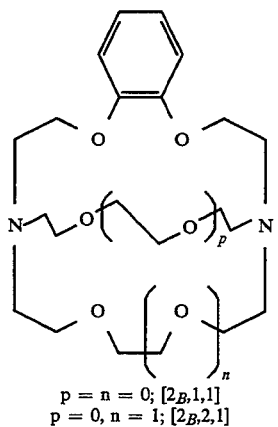

p = n = 0; [2$_B$,1,1]
p = 0, n = 1; [2$_B$,2,1]

The following compounds may be mentioned as preferred phase transfer catalysts:

benzylmethyl ammonium chloride, benzyltributylammonium bromide, benzylammonium chloride, cetylbenzyldimethylammonium chloride, cetylbenzylmethylammonium bromide, dodecyltrimethylammonium chloride, tetrabutylammonium chloride, tetrabutylammonium iodide, triethylbenzylammonium chloride, triethylbenzyl ammonium bromide, 18-crown-6-ether, dibenzo-18-crown-6-ether, dibenzo-24-crown-8-ether, and dicyclohexane-18-crown-6-ether.

Suitable acid-binding agents for carrying out the process according to the invention are customary inorganic and organic bases. The following can preferably be used: hydroxides, carbonates, bicarbonates and alcoholates of alkali metals and of alkaline earth metals, such as sodium hydrogencarbonate, potassium hydrogencarbonate, potassium-tert.-butylate, sodium methylate, sodium carbonate, potassium carbonate, magnesium carbonate, calcium carbonate, lithium hydroxide, sodium hydroxide, potassium hydroxide and calcium hydroxide, and also hydrides, such as calcium hydride, further tertiary amines, such as triethylamine, tributylamine and 1,1,4,4-tetramethylethylene diamine (TMEDA), dialkylamino anilines, such as N,N-dimethylaniline and N,N-diethylaniline, and also cyclic amino compounds, such as pyridine, 4-dimethylamino pyridine (DMAP), 1,4-diazabicyclo[2,2,2] octane (DABCO) and 1,8-diaza-bicyclo[5,4,0]undec-7ene (DBU).

Suitable diluents for carrying out the process according to the invention are all customary inert organic solvents. The following can preferably be used; optionally halogenated aliphatic, alicyclic and aromatic hydrocarbons such as pentane, hexane, cyclohexane, petroleum ether, ligroin, benzene, toluene, xylene, dichloromethane, chloroform, carbon tetrachloride, ethylene chloride, chlorobenzene, dichlorobenzene, and the like; ethers such as ethyl ether, methyl ethyl ether, isopropyl ether, butyl ether, propylene oxide, dimethoxyethane (DME), dioxane, anisole, tetrahydrofurane (THF), diethylene glycol dimethylether (DMG), diethylene glycol diethylether, and the like; ketones such as acetone, methylethyl ketone (MEK), methyl isopropyl ketone, methyl isobutyl ketone (MIBK), and the like; nitriles such as acetonitrile, propionitrile, benzonitrile, and the like; esters such as ethyl acetate, amyl acetate, and the like; acid amides such as N,N-dimethylformamide (DMF), dimethyl acetamide (DMA) and the like; sulfones and sulfoxides such as dimethyl sulfoxide (DMSO), sulfolane and the like; and bases, such as, for example, pyridine.

When carrying out the process according to the invention, the reaction temperature can be varied within a substantially wide range. In general, the process is carried out at temperatures between 0° C. and 150° C., preferably between 0° C. and 100° C.

The process according to the invention is generally carried out under atmospheric pressure. However, it is also possible to carry out the process under reduced or increased pressure.

When carrying out the process according to the invention, 0.5 to 3 mols, preferably 0.8 to 1.2 mols, of ketone of the formula (III) are employed per mol of phenylmethanesulphonyl fluoride of the formula (II). The amounts of acid binding agents can also be varied within a substantially wide range. In general, 1 to 6 mols, preferably 2 to 3 mols, of acid binding agent are employed per mol of phenylmethanesulphonyl fluoride of the formula (II). The amounts of phase transfer catalyst correspond to those which are generally used for organic reactions of this type.

In general, 0.001 to 0.01 mols of phase transfer catalyst are employed per mol of phenylmethanesulphonyl fluoride of the formula (II). - Working-up is carried out by conventional methods.

The 3-phenyl-2-propenones of the formula (I) are valuable intermediates for the preparation of pesticides and pharmaceuticals, particularly for the synthesis of compounds having fungicidal and antimycotic activity (see EP-OS [European Published Specification] 0,040,345). Thus, triazolyl-derivatives of the formula

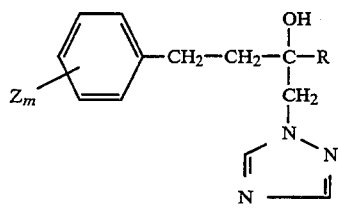

in which

R, Z and m have the above-mentioned meanings,
can be prepared by reacting 3-phenyl-2-propenones of the formula

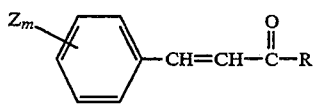

in which

R, Z and m have the above-mentioned meanings,
with hydrogen in the presence of a catalyst, such as Raney nickel, and in the presence of an inert organic diluent, such as xylene or toluene, under a pressure of 5 to 15 bar at a temperature between 50° C. and 100° C., reacting the resulting ketones of the formula

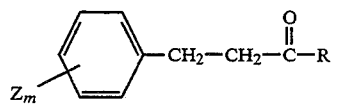

in which

R, Z and m have the above-mentioned meanings,
either

α) with dimethyloxosulphonium methylide of the formula

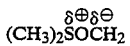

or

β) with dimethylsulphonium methylide of the formula

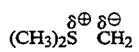

in the presence of an organic solvent, such as tert.-butanol or dimethyl sulphoxide, at a temperature between 10° C. and 60° C., and reacting the resulting oxiranes of the formula

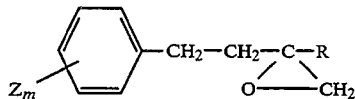

in which

R, Z and m have the above-mentioned meanings,
with 1,2,4-triazole in the presence of an acid binding agent, such as potassium tert.-butylate, and in the presence of a diluent, such as dimethylformamide, at a temperature between 50° C. and 150° C.

The process according to the invention is illustrated by the following examples.

PREPARATION EXAMPLES

EXAMPLE 1

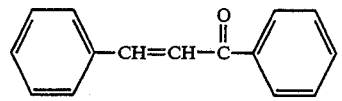

A catalytic amount (about 500 mg) of dibenzo-18-crown-6-ether and 68 g of anhydrous powdered potassium carbonate were added to a solution of 18.4 g phenylmethane-sulphonyl fluoride and 10.0 g of phenacyl bromide in 100 ml of acetonitrile at room temperature, while stirring. The mixture was then stirred under reflux for 10 hours. The reaction mixture was allowed to cool down to room temperature and was then concentrated by stripping off the solvent under reduced pressure. The residue was chromatographed over a silica gel column using toluene as the eluent. The eluate was evaporated. In this manner, 16.0 g of 1,3-di-phenyl-prop-2-en-1-one were obtained in the form of a solid substance of melting point 56° C.

EXAMPLE 2

A catalytic amount (about 300 mg) of tetrabutylammonium bromide and 68 g of powdered anydrous potassium carbonate were added to a solution of 21.8 g 4-chlorophenylmethanesulphonyl fluoride and 23.3 g of 4-chlorophenacyl bromide in 200 ml of tetrahydrofuran at room temperature, while stirring. The mixture was stirred for a further 8 hours at 50° C. The reaction mixture was allowed to cool down to room temperature and was then filtered to remove inorganic substances which had precipitated. The organic phase was concentrated by stripping off the solvent under reduced pressure. The residue was recrystallized from ethanol. In this manner, 19.0 g of trans-1,3-di-(4-chlorophenyl)-prop-2-en-1-one were obtained in the form of yellow crystals of melting point 156° C.

The 3-phenyl-2-propenones of the formula (I) listed in the following Table 1 were also prepared according to the methods given in Examples 1 and 2.

TABLE 1

| $Z_m$ | R | Melting Point (°C.) |
|---|---|---|
| — | $CH_3$ | |
| — | $4\text{-Br}—C_6H_4$ | |
| — | $4\text{-F}—C_6H_4$ | 77 |
| — | $4\text{-Cl}—C_6H_4$ | 98 |
| — | $4\text{-NO}_2—C_6H_4$ | 165 |
| — | $4\text{-CH}_3—C_6H_4$ | 76 |
| — | $3,4\text{-Cl}_2—C_6H_3$ | 115 |
| — | $2,4,6\text{-Cl}_3—C_6H_2$ | 100 |
| — | $2\text{-NO}_2—C_6H_4$ | 129 |
| — | $3\text{-NO}_2—C_6H_4$ | 130 |

TABLE 1-continued

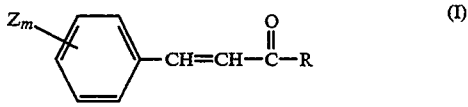

| $Z_m$ | R | Melting Point (°C.) |
|---|---|---|
| — | 2-$CH_3$—$C_6H_4$ | 117–120/0.1 mm Hg (Boiling Point) |
| — | 3-$CH_3$—$C_6H_4$ | 49 |
| — | $(CH_3)_3C$ | 130/13 mm Hg (Boiling Point) |
| 4-Cl | $C_6H_5$ | 115 |
| 4-$NO_2$ | $C_6H_5$ | 165 |
| 4-$CH_3$ | $C_6H_5$ | 95 |
| 4-$NO_2$ | 4-I—$C_6H_5$ | 162 |
| 4-$NO_2$ | 4-Br—$C_6H_4$ | 166 |
| — | $OC_2H_5$ | |

It will be appreciated that the instant specification and claims as set forth by way of illustration and not limitation, and that various modifications and changes may be made without departing from the spirit and scope of the present invention.

We claim:

1. A process for the preparation of a 3-phenyl-2-propenone of the formula

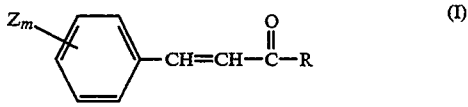 (I)

in which

Z is fluorine, chlorine, bromine, nitro, alkyl with 1 to 4 carbon atoms, halogenoalkyl with 1 or 2 carbon atoms and 1 to 5 halogen atoms, or is cycloalkyl with 5 to 7 carbon atoms, alkoxy with 1 to 4 carbon atoms, halogenoalkoxy with 1 or 2 carbon atoms and 1 to 5 halogen atoms, or is straight-chain or branched alkylthio with 1 to 4 carbon atoms, or halogenoalkylthio with 1 to 2 carbon atoms and 1 to 5 halogen atoms, R is alkyl with 1 to 4 carbon atoms, cycloalkyl with 3 to 7 carbon atoms optionally substituted by 1 to 3 identical or different radicals selected from the group consisting of alkyl with 1 or 2 carbon atoms, or is phenyl which is optionally substituted by 1 to 3 identical or different radicals selected from the group consisting of halogen, nitro, alkyl with 1 to 4 carbon atoms and halogenoalkyl with 1 or 2 carbon atoms and 1 to 5 halogen atoms, and m is 0, 1, 2, 3 or 4, which comprises reacting a phenylmethanesulphonyl fluoride of the formula

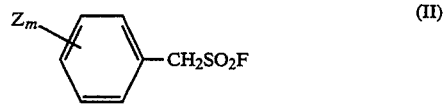 (II)

with a ketone of the formula

 (III)

in the presence of a phase transfer-catalyst selected from the group consisting of a tetraalkyl ammonium halide, benzylalkyl ammonium halide, benzylammonium halide, tetraalkyl phosphonium halide, crown ether and cryptand, and in the presence of an acid binder selected from the group consisting of a hydroxide, carbonate, bicarbonate or alcoholate of an alkali metal or alkaline earth metal, a hydride, tertiary amine, N,N-dialkylamine and cyclic amino compound, and in the presence of an inert solvent selected from the group consisting of an optionally halogenated aliphatic, alicyclic or aromatic hydrocarbon, ether, ketone, nitrile, ester, acid amide, sulfone, sulfoxide, sulfolane and pyridine.

2. A process according to claim 1, in which
R is methyl, ethyl, isopropyl, tert.-butyl, cyclopropyl optionally substituted by 1 to 3 methyl groups, cyclopentyl optionally substituted by 1 to 3 methyl groups, cyclohexyl optionally substituted by 1 to 3 methyl groups, or is phenyl which is optionally substituted by 1 to 3 identical or different radicals selected from the group consisting of fluorine, chlorine, bromine, iodine, nitro, methyl and trifluoromethyl.

3. A process according to claim 1, wherein the reaction is carried out at a temperature between 0° C. and 150° C.

4. A process according to claim 1, wherein m is 0, 1, 2 or 3.

* * * * *